United States Patent [19]

Adell

[11] Patent Number: 5,063,082

[45] Date of Patent: Nov. 5, 1991

[54] METHOD OF MAKING COATED METALLIC ORTHODONTIC ARCH WIRE

[75] Inventor: Loren S. Adell, 6207 Telluride La., Dallas, Tex. 75252

[73] Assignees: Loren Adell; Michael Adell, both of Sunnyvale, Tex.

[21] Appl. No.: 558,709

[22] Filed: Jul. 27, 1990

Related U.S. Application Data

[62] Division of Ser. No. 202,785, Jun. 3, 1988, Pat. No. 4,946,387.

[51] Int. Cl.⁵ .............................................. A61C 7/20
[52] U.S. Cl. ........................................ 427/2; 427/289; 427/409; 427/434.6; 106/35; 433/20; 433/217.1
[58] Field of Search ............... 427/2, 289, 409, 434.6, 427/435; 118/420; 106/35; 433/20, 217.1, 218, 219; 523/115

[56] References Cited

U.S. PATENT DOCUMENTS

| | | | |
|---|---|---|---|
| 3,123,913 | 3/1964 | Rubin | 433/20 |
| 3,838,515 | 10/1974 | Paugh et al. | 433/20 |
| 3,964,165 | 6/1977 | Stahl | 433/21 |
| 4,050,156 | 9/1977 | Chasanoff et al. | 433/20 |
| 4,433,958 | 2/1984 | Fellman et al. | 433/219 |
| 4,659,310 | 4/1987 | Kottemann | 433/20 |
| 4,722,689 | 2/1988 | Corbett | 433/23 |
| 4,731,018 | 3/1988 | Adell | 433/20 |

FOREIGN PATENT DOCUMENTS 2201475 7/1973 Fed. Rep. of Germany ... 433/217.1

OTHER PUBLICATIONS

"Seal Out Dental Decay", U.S. Dept. of Health, Education, and Welfare Publ. No. (NIH) 76-1140 (undated).

Primary Examiner—Shrive Beck
Assistant Examiner—Terry J. Owens
Attorney, Agent, or Firm—George L. Boller

[57] ABSTRACT

A metallic orthodontic wire is coated with a layer of tooth color material and a clear layer of material covers the tooth color material to allow the tooth color material to be seen through the layer of clear material. A preferred material for the tooth color layer is a plastic such as polyethylene or polyurethane. A preferred material for the clear layer is a silicone elastomer.

11 Claims, 3 Drawing Sheets

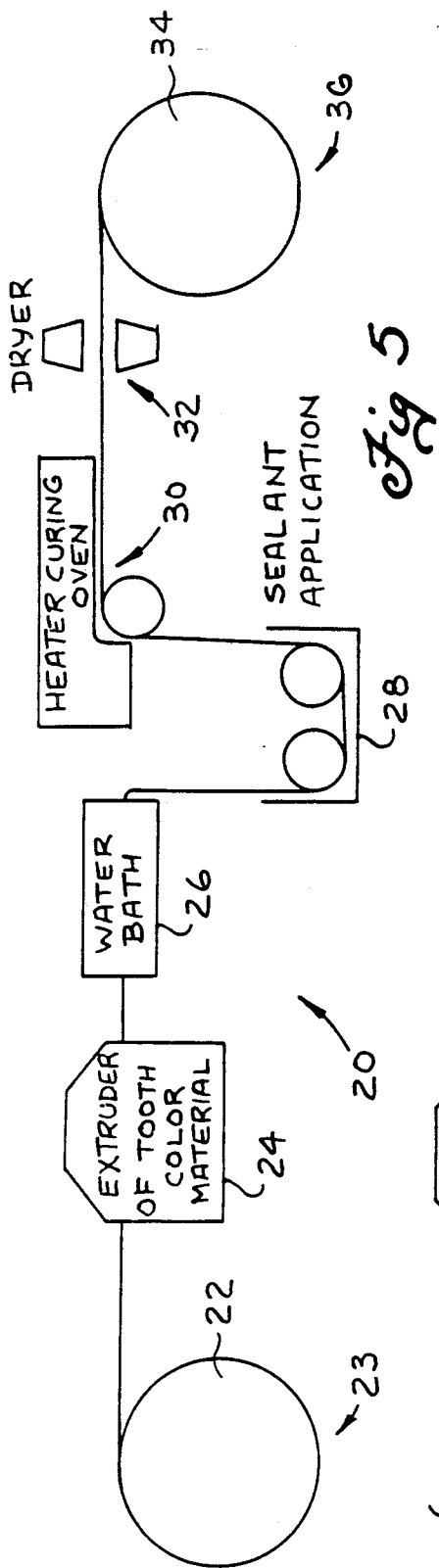
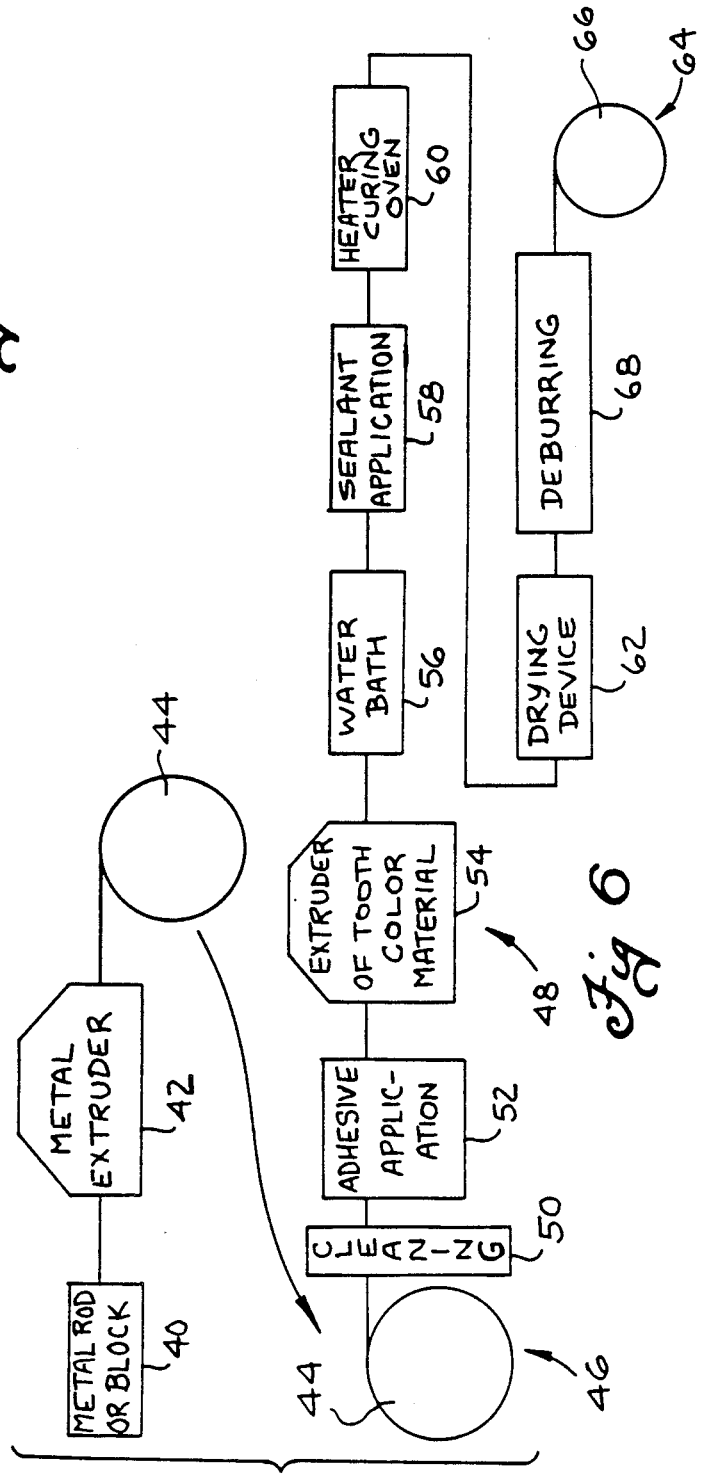

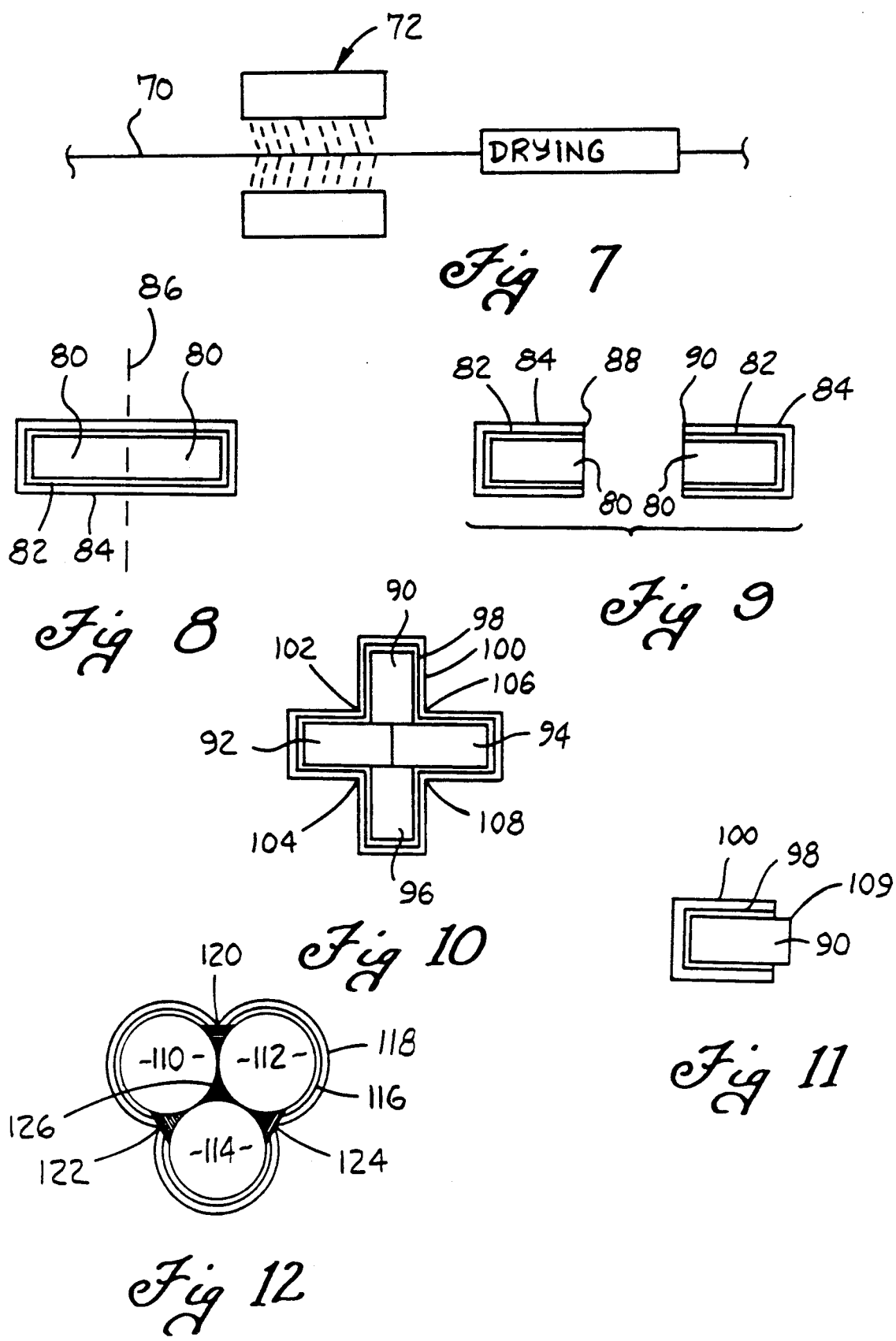

METHOD OF MAKING COATED METALLIC ORTHODONTIC ARCH WIRE

This is a divisional of copending application(s) Ser. No. 07/202,785 filed June 3, 1988, now U.S. Pat. No. 4,946,387.

BACKGROUND AND SUMMARY OF THE INVENTION

This invention relates generally to orthodontic wire and more specifically it relates to a multi-coated orthodontic wire and a method for making such orthodontic wire.

The coating of metallic orthodontic wire with a layer of non-metallic material is known. Examples are shown in the prior art, namely U.S. Pat. No. 4,585,414, as well as in Applicant's own U.S. Pat. No. 4,731,018.

One of the reasons for coating an orthodontic wire, especially an orthodontic arch wire, is to impart to the wire a color that will blend with teeth of the arch when the arch wire is in use. In this way the arch wire is made relatively inconspicuous, a desirable attribute for appearance.

The present invention relates to an orthodontic wire which is constructed in a new and unique way to present an appearance corresponding to that of tooth color so that as an arch wire, it will be rendered relatively inconspicuous.

Prior coated orthodontic wires contain coloration in the coating material that matches the tooth color. If this material is worn away, the bare metal becomes exposed.

The present invention is directed to a new and unique construction for an orthodontic wire which will provide improved quality for the maintenance of tooth coloration. According to a preferred embodiment of the present invention, a very thin layer of tooth color material is applied to the metal wire. This thin layer of tooth color material is then covered by an overlying clear protective layer. In this way the tooth color material can be selected for its desired coloration, and ease of its attachment or bonding to metal wire, without major concern for its inherent resistance to wear. Wear resistance and durability are imparted by the clear overlying protective layer with the result that the dual attributes of desired tooth color appearance and durable exterior are achieved in an orthodontic wire that is predominantly metallic.

Related aspects of the invention involve various methods by which the described orthodontic wire is fabricated. Where a metal wire of circular cross section is to be coated by passing the wire through a processing line that applies the coatings, it is been found important to keep the wire from twisting; according to a further aspect of the invention, a lip, or protuberance, is provided at a given location on the circumference of the wire to act as a locator for accurately circumferentially locating the wire with respect to the process line as it passes through. After the coating operations have been completed, this protuberance and the portions of the coatings which overlie it are removed, thereby leaving a partially coated arch wire. The partial coating extends around a majority of the circumference of the wire so that exposed metal is along a limited circumferential region. This type of wire is especially useful in the practice of applicant's invention as described in U.S. Pat. No. 4,731,018 where a limited circumferential region of the arch wire is intentionally left as bare metal to provide a better joint with an orthodontic bracket that receives the arch wire. Although the present invention is especially useful for fabricating orthodontic wire to be used as orthodontic arch wire, the dual coated orthodontic wire of the present invention may be used for fabricating other wire type orthodontic devices, such as a ball clasp for example.

The foregoing features, advantages, and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

BRIEF DESCRIPTION OF THE DRAWINGS

FIG. 5 is a schematic diagram of a process line for fabricating orthodontic wire according to principles of the invention.

FIG. 6 is a schematic diagram of a second embodiment of process line for fabricating orthodontic wire according to the present invention.

FIG. 7 is a partial schematic view of a process line illustrating an alternate embodiment.

FIGS. 8 and 9 are end views of orthodontic wires exemplifying still further principles of the invention.

FIGS. 10 and 11 are end views of orthodontic wires exemplifying still further principles of the invention.

FIGS. 12 is an end view of orthodontic wires exemplifying even further principles.

DESCRIPTION OF THE PREFERRED EMBODIMENT

Figure 1:
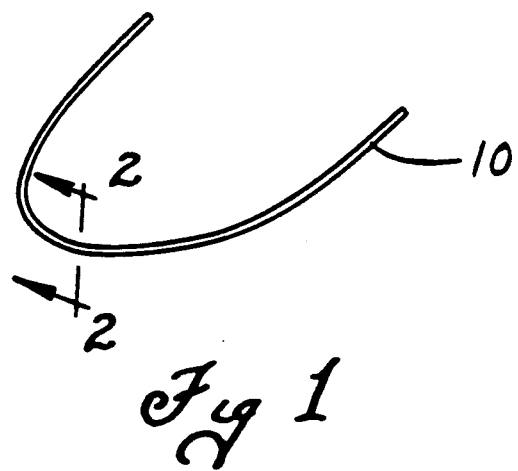
FIG. 1 is a perspective view of an orthodontic arch wire embodying principles of the invention.
Figure 2:
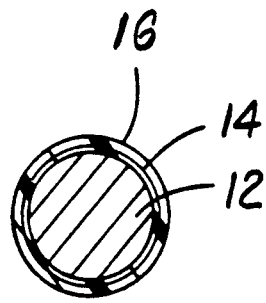
FIG. 2 is an enlarged transverse cross sectional view taken in the direction of arrows 2—2 in FIG. 1.

FIG. 1 and 2 show a generally U-shaped orthodontic arch wire 10 embodying principles of the present invention. Arch wire 10 comprises a metal wire 12 that has a circular cross section. According to the inventive principles, a layer of tooth color material 14 is applied to, and in the illustrated embodiment extends around the full circumference of, arch wire 12. The layer of tooth color material 14 is in turn covered by a clear protective layer 16, which like layer 12 extends fully circumferentially around layer 14. The layers 14 and 16 are circular annular in shape so that the resulting overall cross section of arch wire 10 is of circular shape like wire 12, but slightly larger.

Wire 12 may be a conventional sized arch wire of typical arch wire metal. The preferred layer 14 can be any of a several materials. It can be a very thin layer of a suitable paint, such as an elastomeric paint, or a thin layer of a suitable plastic, such as polyethylene or polyurethane. Such materials can be bonded by conventional procedures to the arch wire metal so that they will elongate with the metal when the metal is bent to a desired shape. The layer need only be thick enough so that the desired tooth color appearance is presented.

The layer 16 is a protective layer that serves to encapsulate tooth color layer 14 while permitting the color of layer 14 to be presented through the layer 16. A preferred material for layer 16 is a pharmaceutical grade of clear silicone elastomer (silicone). The thickness of layer 16 is made just thick enough to protect the tooth color material against various mechanical and chemical effects that the arch wire will be subjected to when in use. The coating 16 also has the ability to elongate with the metal when the arch wire is formed into desired shapes. In this regard silicone has good elastomeric properties. For intra-oral use, silicone is quite inert to chemical influences, and it possesses satisfactory abrasion-resistance.

Figure 3:
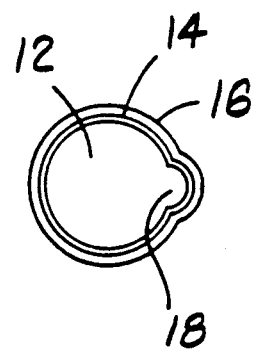
FIG. 3 is an end view similar to FIG. 2 but illustrating an alternate embodiment.

FIG. 3 shows the transverse shape of another embodiment of arch wire that contains a metal wire 12, and coatings 14 and 16 similarly organized and arranged with respect to wire 12. The embodiment of FIG. 3 differs in that the metal wire 12 includes a small lip, or protuberance, 18 that interrupts the otherwise circular cross section. The coatings 14 and 16 have similar lips covering lip 18. Lip 18 extends continuously lengthwise of the wire. As will become apparent from a detailed description of the manufacturing process later on, this lip serves to circumferentially locate the metal wire during the process of applying the coatings 14 and 16.

Figure 4:
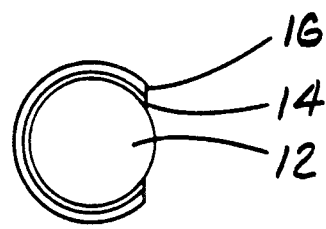
FIG. 4 is a view similar to FIG. 3 after further processing.

After the coatings have been applied to the wire of FIG. 3, the protuberance 18, and those portions of the coatings 14 and 16 covering it, are removed to yield the transverse cross sectional shape in FIG. 4. Removal can be accomplished by cutting or other equivalent procedures. As can be seen from FIG. 4, bare metal is exposed over a portion of the circumference of the wire where the protuberance previously was. The remainder of the wire remains circular in cross section and remains covered by layers 14 and 16. This embodiment of wire is especially advantageous for use in the practice of the invention disclosed in applicant's patent U.S. Pat. No. 4,731,018 issued Mar. 15, 1988. When the wire is put to use as an arch wire, the exposed metal portion of the wire faces teeth of the arch while the covering layers 14 and 16 face labially. When the arch wire is placed in association with brackets on teeth of the arch, the exposed metal of the wire provides direct contact of the arch wire metal with the brackets without intervention by layers 14 or 16. Yet the desired coloration is presented labially so that the arch wire presents a tooth color appearance blending with the teeth of the arch. Further details of the invention U.S. Pat. No. 4,731,018 may be had by reading that patent.

FIG. 5 illustrates a process line 20 for fabricating the arch wire embodiment of FIG. 2. A coil of bare metal orthodontic wire 22 of suitable size is placed at an uncoiling station 23 and uncoiled. The wire is conducted through an extruding station 24 at which the tooth color material layer 14 is extruded onto the wire. Where the extruded material is a plastic such as polyethylene or polyurethane, the extruded plastic is hot as it leaves the extruder and therefore must be cooled by passing through a water bath 26.

From water bath 26, the metal wire containing coating 14 is conducted to a sealant application station 28 where the outer coating layer 16 is applied. The illustrated process shows the coated wire material being guided through a bath of liquidfied silicone which will adhere to the coating 14. From station 28, the material is conducted to a curing oven 30 which cures the silicone coating to a stable state. From there, the multi-coated wire is passed through a drying device 32 and is finally coiled into a coil 34 at a coiling station 36.

The process is a continuous one to produce coils of desired lengths of wire. The finished coils are then available for use in fabricating various orthodontic devices containing orthodontic wire. Examples are arch wires and ball clasps, already mentioned. The wire is pulled through the process line at a generally constant speed. The extruder is operated in accordance with the speed of the wire to extrude the layer 14 at an appropriate thickness onto the wire as the wire passes through the extruder. The amount of time that the wire is in the sealant bath 28 will be long enough to provide a suitable thickness for the cured sealant coating after passing through curing oven 30.

The resulting product possesses the appearance of tooth color due to layer 14 which can be clearly seen through the transparent coating 16. The transparent layer 16 provides a strong, durable layer for protecting the tooth color layer 14. Although the process of FIG. 5 portrays a round orthodontic wire, it is to be appreciated that other cross sections may be fabricated in accordance with the same principles.

FIG. 6 illustrates a process for making the embodiment of FIG. 3. A rod or block of suitable metal 40 is passed through a metal extruder 42 to create a coil 44 of bare wire in which the cross section of the metal is like that shown in FIG. 3 containing the general circular transverse cross sectional shape but with the protuberance 18. A coil 44 is then set up at the uncoiling station 46 of a process line 48.

First, the wire is passed through a cleaning station 50 where the wire's exterior is thoroughly cleaned so that it can receive adhesive that is applied at the next station 52. Station 52 applies to the full circumference of the metal wire, including the protuberance, a thin adhesive coating. The adhesive coated wire next passes through an extruding station 54 at which the tooth color material is extruded onto the adhesive. The next several steps of the process are like those described in FIG. 4, consisting of a water bath 56, a station 58 for applying the transparent outer coating 16, a curing oven 60, and a drying device 62. Before the coil of finished wire 66 is wound at a coiling station 64, the protuberance 18 and overlying layers 14, 16 are removed, such as by a deburring or other similar techniques. The numeral 68 designates this step. The wire in the finished coil has the transverse shape shown in FIG. 3. During passage of the wire through the line, protuberance 18 served as a circumferential locator to keep the wire from twisting, but thereafter the protuberance becomes unnecessary.

It is deemed desirable to utilize adhesive between the tooth coating material and the metal, particularly where the coated wire is processed to produce a region of bare metal, such as by the removal of protuberance 18 and of the overlying portions of layers 14 and 16. The unremoved portions of the overlying layers 14 and 16 do not fully circumferentially cover the metal wire; rather the layers will have edges of termination, running parallel to the length of the wire, that define the boundaries of the exposed metal region of the wire. Adhesive is desirable for resisting any tendency of the underlying layer 14 to separate from the metal, particularly along these exposed edges of the layer.

FIG. 7 illustrates a modification that can be made to a portion of the process line of either FIGS. 5 or 6. The wire which already contains the tooth color material is designated by the reference numeral 70. The station 28 is replaced by a spraying station 72 at which the coating 16 is applied by spraying. Thereafter the coated wire passes through the drying procedure as it travels toward completing the process. Thus, there are various ways to apply coating 16, rolling it on is another way, and it is also to be appreciated that there are various ways to apply coating 14. For example, instead of using an extrusion process to apply the layer 14 to wire 12, it is contemplated that powder coating procedures could be used, such as through the use of electrostatic apparatus, fluidized beds, or cloud chambers. Injection molding and flame coating are other means for depositing plastic onto the metal wire.

Using silicone for the outer layer 16 endows that layer with a tenacity for the underlying layer 14, but it is to be appreciated that in certain instances it may be appropriate to use adhesive between these two layers. As such, the process lines could include an adhesive applying station immediately preceding the station that applies the outer coating 16. It is also contemplated that procedures such as laminating could be used, for example where the sealant material that forms the outer layer 16 is applied by a laminating or a shrink fit process.

FIGS. 8 and 9 portray another method for making coated metallic orthodontic wire in which a limited region of the wire is bare metal. In FIG. 8 a pair of metal wires 80 that are rectangular in transverse cross sectional shape are placed side-by-side and then coated around the outside with a tooth color layer 82 and with a clear transparent outer protective layer 84 according to the processes previously described. Subsequently the two are severed from each other along a plane of severing 86 to yield the two separate orthodontic wires 88 and 90 shown in FIG. 9. Each of the two wires 88, 90 has a bare metal surface along one of the shorter sides of the metal. The remainder of each arch wire is covered by the multiple coatings 82, 84.

In use as an arch wire, each of the wires 88, 90 will have the exposed bare metal bearing against a bracket so that the metal of the arch wire is in direct contact with the bracket while the covering layers face liabally so that the tooth color layer 82 can be seen through the clear protective layer 84 thereby blending the arch wire to the color of teeth of the arch. The two metal wires could alternatively be formed from a one-piece strip that is severed along the plane 86 during the severing operation.

FIGS. 10 and 11 illustrate another method of making the multiple coated wire. Here four individual rectangular shaped wires 90, 92, 94 and 96 are bundled together in the cruciform manner shown. The bundled wires are passed through a process line such as those of FIGS. 5-7 to cause the entire exterior of the bundled wires, as viewed in transverse cross section, to be coated with the tooth color layer 98 and with the clear overlying protective layer 100. The covering layers are slit at, or immediately adjacent, the four corners indicated by the reference numerals 102, 104, 106, 108 thereby separating the bundle into four individual wires each of which contains a coated region and an uncoated region. A representative transverse shape for one of the individual arch wires 109 is shown in FIG. 11. One of the shorter sides of the metal wire is bare as are the immediately contiguous margins of the two adjacent longer sides. The remainders of these longer sides as well as the other shorter side of the metal wire are covered by the layers 98, 100.

FIG. 12 shows three circular metal wires of equal diameter 110, 112, 114 placed together so that each has two points of tangency with the other two. The bundled wires are passed through a process line such as those shown in FIGS. 5-7 and the entire exterior transverse cross section is coated with a tooth color layer 116 and a clear protective layer 118 except at the three locations 120, 122, 124. After coating the bundle is separated into the three individual wires. The circumference of each wire has a bare metal region while the remainder is a region that is covered by the overlying layers 116, 118. The areas indicated by the reference numerals 120, 122, 124, as well as the reference numeral 126, are not covered during the extrusion process and to accomplish this the extrusion die may be suitably constructed with wedges or fillers that prevent extruded material from entering these regions. In any event, excess material that may intrude into a region that is intended to be left bare metal can be subsequently removed by conventional procedures. When the three wires that result from the process of FIG. 12 are used as arch wires, each will be exposed along a limited region of its circumference that is to be placed against an orthodontic bracket while the remainder of the circumference will face labially to present an appearance matching tooth coloration.

Relatively modest thickness for the layers 14, 16 are quite satisfactory. Layer 14 can be 0.003 inch or less, and layer 16 can be 0.002 or less. The metal wire can be of any of the typical shapes and sizes that are used for orthodontic wire.

While a preferred embodiment of the invention has been disclosed, it will be appreciated that principles are applicable to other embodiments.

What is claimed:

1. A method of making coated metallic orthodontic wire which comprises passing metal wire sequentially through plural processing stations, applying to the metal wire at a first of said stations a layer of tooth color material that presents a color simulating that of teeth with which the orthodontic wire is adapted to be used, and applying at a second of said stations a layer of clear material covering said layer of tooth color material to protect said layer of tooth color material in an intra-oral environment while allowing the color of the layer of tooth color material to be presented through the layer of clear material.

2. A method as set forth in claim 1 including the step of subsequently removing a selected portion of both said layers from a limited region of the periphery of the metal wire so as to expose a portion of the metal wire.

3. A method as set forth in claim 2 in which said metal wire has a generally circular cross section but contains a protuberance at a given circumferential location for maintaining proper circumferential alignment of the wire as it passes through said stations and wherein the step of subsequently removing both layers from a limited region of the periphery of the metal wire is conducted at the region of said protuberance and includes removing said protuberance.

4. A method of making coated metallic orthodontic wire which comprises passing metal wire through a process line which coats the wire with full encapsulation as viewed in transverse cross section, and after the coating has been applied to the metal wire, axially severing at least the coating at plural locations around the periphery of the coated wire to yield at least one coated metal wire whose circumference is partially coated and partially bare metal.

5. A method as set forth in claim 4 in which the metal wire which passes through the process line comprises a bundle of plural metal wires.

6. A method as set forth in claim 5 in which the bundle of plural wires is arranged to comprise two rectangular metal wires placed side-by-side.

7. A method as set forth in claim 5 in which said bundle of plural wires is arranged to comprise four rectangular metal wires in a cruciform shape.

8. A method as set forth in claim 5 in which said bundle of plural wires is arranged to comprise three circular metal wires arranged such that the circumference of each of the three wires is substantially tangent to that of the other two.

9. A method as set forth in claim 4 in which the metal wire is a single wire that is severed along with the step of severing the coating to yield at least two partially coated and partially bare orthodontic wires.

10. A method of making coated metallic orthodontic wire which comprises passing through a process line a metal wire that has a generally circular shape that contains a protuberance at a particular circumferential location on its periphery as viewed in transverse cross section, applying coating material to fully coat the metal wire as viewed in transverse cross section, and subsequently removing the protuberance and the overlying portions of the coating material to yield a wire in which the periphery is partially coated and partially bare metal.

11. A method as set forth in claim 10 in which the coating material is applied as two layers, one at a first station and another at a second station, and wherein the layer applied at the first station is a tooth color material and the layer that is applied at the second station is a clear material covering the layer of tooth color material.

* * * * *